United States Patent
Stoner et al.

(10) Patent No.: US 8,879,059 B2
(45) Date of Patent: Nov. 4, 2014

(54) METHODS AND APPARATUS FOR CONTROLLED GENERATION OF HYPERFINE POLARIZATIONS AND COHERENCES

(75) Inventors: Richard E. Stoner, Framingham, MA (US); Joseph M. Kinast, Cambridge, MA (US); Antonije Radojevic, Arlington, MA (US); Brian P. Timmons, Milford, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 451 days.

(21) Appl. No.: 13/398,390

(22) Filed: Feb. 16, 2012

(65) Prior Publication Data

US 2013/0215421 A1  Aug. 22, 2013

(51) Int. Cl.
*G01J 3/44* (2006.01)
*G01N 21/65* (2006.01)
*G01V 7/00* (2006.01)

(52) U.S. Cl.
CPC . *G01N 21/65* (2013.01); *G01V 7/00* (2013.01)
USPC ........................................................ 356/301

(58) Field of Classification Search
CPC ............. G01C 19/62; G01P 3/50; G01V 7/00
See application file for complete search history.

(56) References Cited

U.S. PATENT DOCUMENTS 6,314,809 B1 * 11/2001 Kasevich et al. ........... 73/382 R
7,501,906 B2 * 3/2009 Dimarcq et al. ............ 331/94.1

OTHER PUBLICATIONS

N. Yu, "Development of an atom-interferometer gravity gradiometer for gravity measurement from space" Jul. 18, 2006.*
Fritz Ehlotzky,"Atomic phenomena in bichromatic laser fields", Apr. 2000.*
C.S. Adams, "Laser cooling and Trapping of Neutral atoms", 1997.*
Hiromitsu Imai,"Evaluation of the geometric phase of a two-level atom manipulated on the Bloch sphere using a time-domain atom interferometer" Jul. 23, 2007.*

* cited by examiner

*Primary Examiner* — Kara E Geisel
*Assistant Examiner* — Maurice Smith
(74) *Attorney, Agent, or Firm* — Lando & Anastasi, LLP.

(57) ABSTRACT

Methods and apparatus that provide for precise and continuously-controlled generation of hyperfine polarizations and coherences in samples of laser cooled atoms. In one example, coherent population trapping induced by Raman pulses with preselected parameters (such as phase and duration) is employed as a mechanism for producing well-controlled atomic coherences and polarizations. In one example, these coherences and polarizations are used to provide precision polarization references for normalization of polarization readout measurements, and/or to provide precision phase references for phase storage or phase comparison.

15 Claims, 9 Drawing Sheets

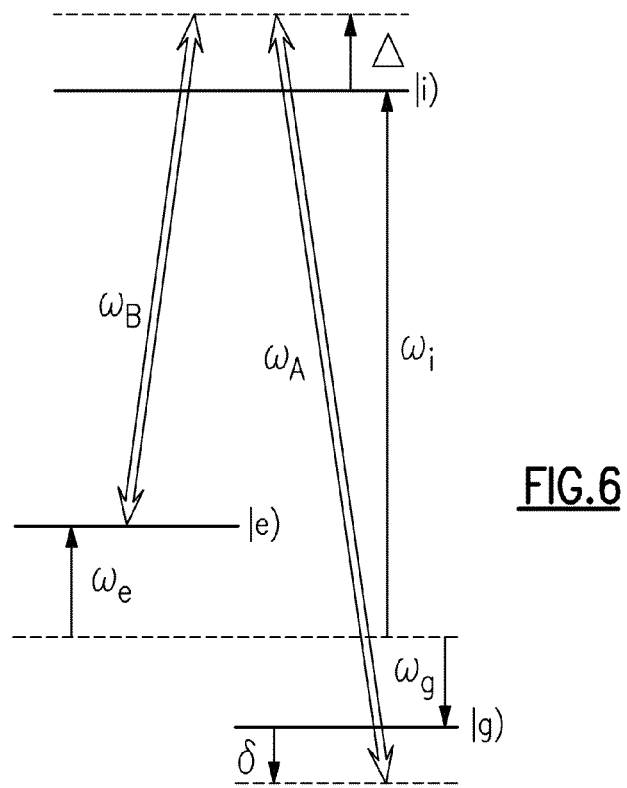
FIG. 6
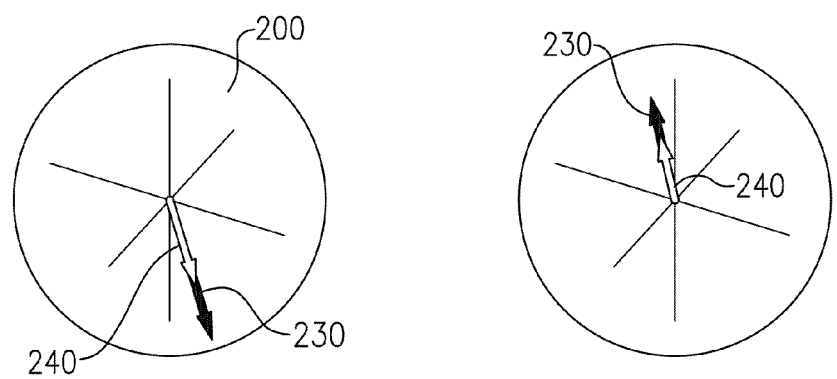
FIG. 7A
FIG. 7B

METHODS AND APPARATUS FOR CONTROLLED GENERATION OF HYPERFINE POLARIZATIONS AND COHERENCES

BACKGROUND

Atom interferometry is used to provide sensitive measurements of inertial forces for inertial navigation and geophysical applications. At present, state of the art atom interferometer inertial sensors involve light pulses rather than mechanical gratings for coherent manipulation of matter waves. Many implementations of light pulse atom interferometers use stimulated Raman transitions as the atom beamsplitter and mirror. While other light pulse beamsplitters, such as multi-photon Bragg pulses and Bloch oscillations, may achieve larger momentum transfer and thus offer higher interferometer sensitivity, Raman pulse beamsplitters are relatively simple to implement and place less stringent requirements on atom temperature and laser power.

Referring to FIG. 1, in a Raman pulse beamsplitter, a bichromatic (two frequencies) laser field 110 drives stimulated Raman transitions in cold atoms 120. The laser field affects the population distribution of the cold atoms, and allows effects of interest to be measured. Atom interferometry relies on the presence of known initial conditions, specifically, a polarized atom cloud. Optical pumping is used to create polarized atom samples, and Raman pulses may be applied to such polarizations to create atomic coherences. However, the phase of the resulting coherence can deviate from the phase of the drive field in an uncontrolled fashion, because of frequency tuning error of the drive, AC Stark shifts of the atomic resonance, or other spurious resonance shifts.

SUMMARY OF INVENTION

Aspects and embodiments are directed to methods and apparatus that allow precise and continuously-controlled generation of hyperfine polarizations and coherences in samples of laser cooled atoms. In particular, as discussed below, aspects and embodiments employ coherent population trapping through applied Raman pulses as a highly controllable mechanism for producing hyperfine atomic coherences and polarizations. These coherences and polarizations may be exploited to provide precision polarization references for normalization of polarization readout measurements, and/or to provide precision phase references for phase storage or phase comparison, as discussed further below. A mechanism for producing a coherence of precise phase and known amplitude using the same electro-optics hardware suite as used for Raman pulses may provide a precision polarization "yardstick" for Raman pulse atom interferometry.

According to one embodiment, a method of generating controlled hyperfine polarizations in a sample of cold atoms comprises applying a first Raman pulse having a first predetermined duration and phase to induce a coherence aligned with an effective drive field vector of the first Raman pulse, after a predetermined dwell time, applying a second Raman pulse having a second predetermined phase that is ±90 degrees relative to the first predetermined phase to rotate the induced coherence perpendicular to the effective drive field vector of the first Raman pulse, and measuring the induced coherence as a population difference.

In one example of the method, applying the first Raman pulse includes selecting the first predetermined phase based on a desired phase of the induced coherence, and selecting the first predetermined duration based on a desired amplitude of the induced coherence. The first predetermined duration may be at least ten $\pi$ pulse durations, and the predetermined dwell time may less than a lifetime of the induced coherence, for example. In another example, applying the second Rama pulse includes applying a $\pi/2$ Raman pulse. The first and second Raman pulses may be applied using a bichromatic laser field. In one example, applying the first and second Raman pulses includes applying velocity insensitive Raman pulses. In another example, a laser difference for the first Raman pulses is different than a laser difference frequency for the second Raman pulse. In another example, applying the first and second Raman pulses includes applying velocity sensitive Raman pulses.

Another embodiment is directed to a method of generating a precise polarization having a desired phase and magnitude from an initially unpolarized cold atom cloud, the method comprising applying a Raman pulse having the desired phase to the atom cloud for a duration sufficient to produce an effective drive field and induce the precise polarization via coherent population trapping.

In one example, applying the Raman pulse includes applying a velocity insensitive Raman pulse. In another example, applying the Raman pulse includes applying a velocity sensitive Raman pulse. Applying the Raman pulse may include selecting a laser detuning frequency and laser detuning phase of the Raman pulse to achieve a desired orientation of the effective drive field.

According to another embodiment, a method of providing a normalized population readout in a two-state quantum system comprises applying a first Raman pulse having a first phase to the quantum system to induce precession of an initial polarization and to induce a first polarization via coherent population trapping, during the first Raman pulse, measuring a z-component of the initial polarization of the quantum system using a probe to obtain a first relative amplitude of the initial population and to dephase the initial population, applying a second Raman pulse having a second phase that is ±90 degrees relative to the first phase to rotate the first polarization, measuring a z-component of the first polarization using the probe to obtain a second relative amplitude of the first polarization, comparing the first and second relative amplitudes, and determining a magnitude of the initial polarization of the quantum system based on the comparison and on a known relationship between parameters of the first and second Raman pulses and a magnitude of the first polarization. In one example, applying the first Raman pulse includes applying a Raman pulse having a duration of at least ten $\pi$ pulse durations.

Still other aspects, embodiments, and advantages of these exemplary aspects and embodiments, are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the invention. In the figures, each identical or nearly identical component that is illustrated in various figures is represented by a like numeral. For purposes of clarity, not every component may be labeled in every figure. In the figures:

FIG. 6 is a diagram of a three-level (Λ) atom and laser fields;

FIG. 7A is a diagram of a Bloch sphere including a coherence induced by an applied effective drive field according to aspects of the invention;

FIG. 7B is a diagram of a Bloch sphere including a coherence and a polarization induced by an applied effective drive field according to aspects of the invention;

DETAILED DESCRIPTION

Aspects and embodiments are directed to systems and methods for precise and continuously controlled generation of hyperfine polarizations and coherences in laser-cooled atoms. Precise polarizations may provide a measurement "yardstick" for measuring fractional ground state populations in ultracold atom samples. An atomic coherence is the induced coherence between levels of a multi-level atomic system observed when the system interacts with a coherent electromagnetic field. Precise coherences may be useful because their phase with respect to the generating radio frequency (RF) source is well defined, independent of whether the frequency of the RF source is resonant with the atom's hyperfine splitting. The ability to generate a continuum of precise polarization and coherence values is directly applicable to precision inertial sensing and timekeeping using cold atoms.

According to one embodiment, coherent population trapping (CPT), or the transfer of atomic population to a decoupled (dark) superposition state, induced by Raman pulses in light pulse atom interferometers is employed as a mechanism for producing well-controlled atomic coherences and polarizations. In one embodiment, Raman pulses are used to trap population in a dark, coherent superposition of two ground state hyperfine energy levels, which produces systematic phase shifts in atom interferometers, as discussed further below.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiment.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 2A:
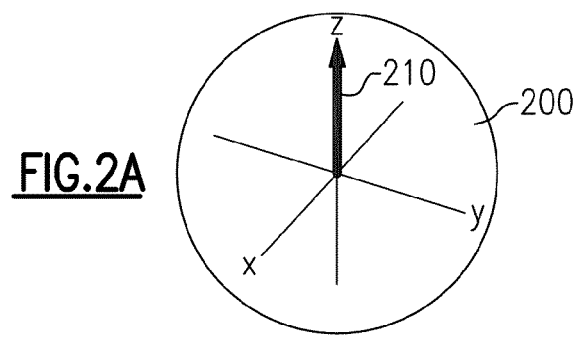
FIG. 2A is a diagram of a Bloch sphere representing a two-level quantum system purely in a first state.
Figure 2B:
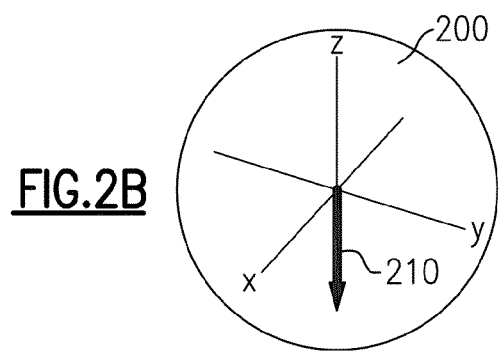
FIG. 2B is a diagram of a Bloch sphere representing the two-level quantum system purely in a second state.
Figure 2C:
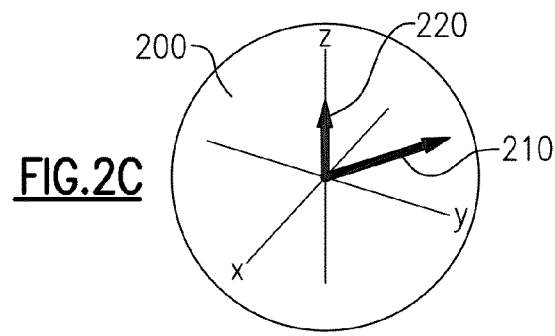
FIG. 2C is a diagram of a Bloch sphere representing the two-level quantum system in a mixture of the two states.

Quantum systems may be complex, featuring a large number of quantum states and complicated dynamics by which the quantum system changes from one state to another. However, many of these highly complex quantum systems can be manipulated in such a way that only two quantum states are in play. These "two-level" systems form the basis of many technologies based on quantum systems, such as atomic clocks, for example. One technique for visualizing two-level quantum systems uses the so-called Bloch sphere. Consider a two-level quantum system in which the two states are referred to as "A" and "B." The Bloch sphere provides a mechanism by which to indicate the probability of the quantum system occupying either state A or state B. This information is represented by the orientation of a state vector relative to the z-axis of the Bloch sphere. For example, referring to FIG. 2A, a quantum system purely in state A is represented by a state vector 210 pointing along the +z axis on the Bloch sphere 200. In FIG. 2B, the system is purely in state B and is represented by the state vector 210 pointing along the −z axis on the Bloch sphere 200. In FIG. 2C, the system is in a mixture of states A and B, and the projection of the state vector 210 along the z-axis (arrow 220) indicates that the system is more likely to be in state A than in state B.

Figure 3A:
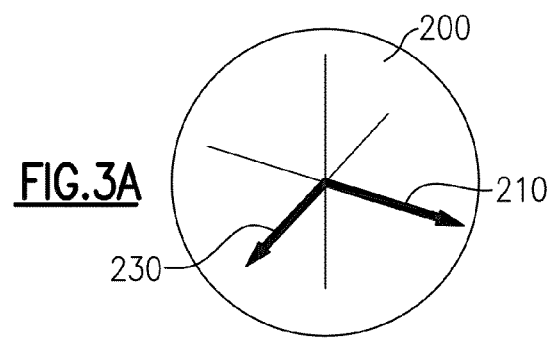
FIG. 3A is a diagram of the Bloch sphere illustrating an example of an applied effective drive field.
Figure 3B:
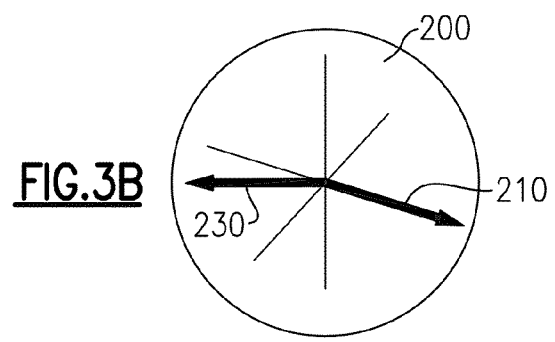
FIG. 3B is a diagram of the Bloch sphere illustrating another example of an applied effective drive field.

In addition to representing information about state populations, the Bloch sphere may be used to represent other quantum correlations, or coherences. This information is encoded in the projection of the state vector 210 in the x-y plane on the Bloch sphere 200. As the quantum system is manipulated, the probability that it occupies states A and B can be altered, and the coherences may be altered as well. In one embodiment, the manipulation applied to the quantum system may be represented on the Bloch sphere 200 by an effective drive field vector. For example, referring to FIG. 3A, there is illustrated an example of an effective drive field 230 applied along the +x axis on the Bloch sphere 200. FIG. 3B illustrates the effective drive field 230 pointing in an arbitrary direction. The phase of the drive field determines how the effective drive field 230 projects onto the x-y plane. The detuning of the effective drive field 230 determines its projection onto the z-axis. In general, both the phase and the detuning of the effective drive field 230 may be controlled with great precision.

A two-level quantum system with no coherences and no preferred probability of occupying one state or the other may be represented with an "empty" Bloch sphere (i.e., no state vector 210 present). The system is said to be "unpolarized" in this case.

Figure 4A:
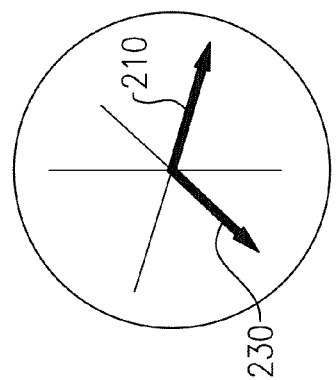
FIGS. 4A-4D are diagrams of the Bloch sphere illustrating induced rotation of the state vector about the effective drive field vector during application of a Raman pulse according to aspects of the invention.
Figure 4B:
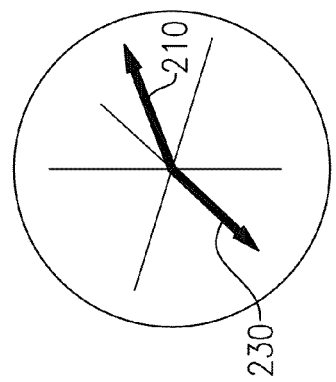
Figure 4C:
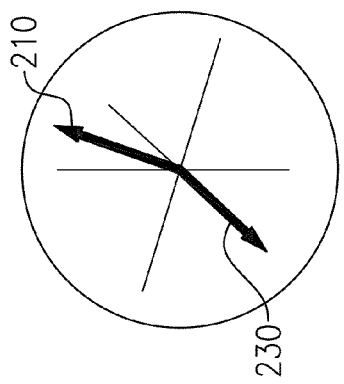
Figure 4D:
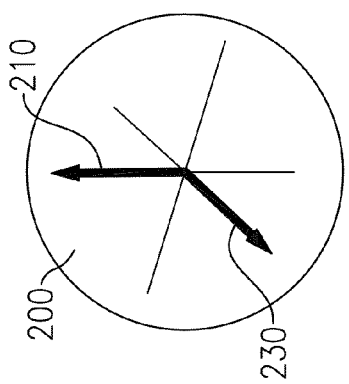
Figure 5D:
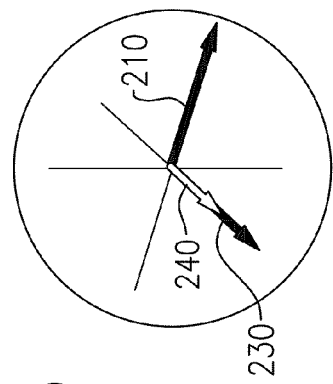
FIGS. 5A-5D are diagrams of the Bloch sphere, corresponding to FIGS. 4A-4D, and illustrating generation of a coherent population trapping-induced coherence during application of the Raman pulse according to aspects of the invention.
Figure 5C:
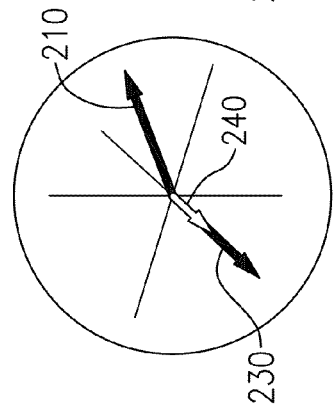
Figure 5B:
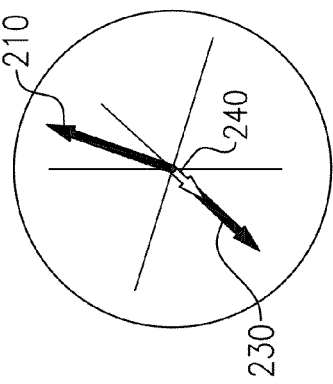
Figure 5A:
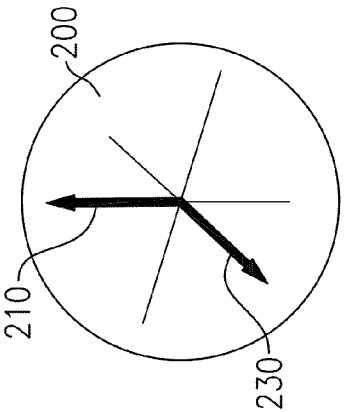

According to one embodiment, a Raman pulse is used to create the effective drive field with which to manipulate a quantum system that comprises cold atoms. As demonstrated below, application of the Raman pulse to the quantum system "torques" the state vector about the effective drive field. For example, referring to FIGS. 4A-4D, consider the quantum system initially in state A (FIG. 4A) at the start of pulse. As the pulse is applied, the state vector rotates toward the x-y plane, as shown in FIGS. 4B and 4C. At the end of the pulse, the quantum system is equally likely to be found in state A or B (FIG. 4D). Thus, by applying a known effective drive field, the system can be "polarized" in a known manner. In particular, as discussed further below, application of the Raman pulse introduces a polarization that is aligned with the effective drive field vector 230. In addition, during application of the Raman pulse, coherent population trapping occurs, and its effect is to generate a coherence that is oriented along the effective drive field vector 230. This effect is illustrated in FIGS. 5A-5D, which correspond to FIGS. 4A-4D, only showing the coherence 240 generated by coherent population trapping during the Raman pulse.

Coherent population trapping has been extensively analyzed and observed experimentally in three-level ($\Lambda$) atomic systems with Raman resonances excited by bichromatic laser fields. However, conventional analyses of stimulated Raman transitions commonly neglect the effects of spontaneous emission, or treat it solely as a source of decoherence. According to one embodiment, a density matrix theory is presented that can be used to calculate Raman pulse output state amplitudes and which, by including the effects of spontaneous emission during the Raman pulse, predicts coherent population trapping effects. Accordingly, the CPT coherences induced by a Raman pulse beam splitter may be accurately controlled by controlled application of the effective drive field, as discussed further below.

According to certain embodiments, a density matrix for a three-level atom is provided and used to compute output state amplitudes. The derivation includes spontaneous emission as a loss term in the equation of motion for the atomic density matrix. After adiabatically eliminating the excited state, the reduced density matrix may be represented as an atomic pseudospin on a Bloch sphere, and the resulting equation of motion for this vector is shown to include the formation of dark state coherences in addition to the standard result of a pseudospin precessing about an effective drive field vector.

Referring to FIG. 6, there is illustrated a diagram of a three-level ($\Lambda$) atom with two closely-spaced ground states $|g\rangle$ and $|e\rangle$, and a single excited state $|i\rangle$. The two ground levels are coupled by two coherent light fields, $\vec{E}_A$ and $\vec{E}_B$, defined according to Equation (1) below:

$$\vec{E}_j = E_j \exp(i(w_j t - \vec{k}_j \cdot \vec{r} + \phi_j)) \qquad (1)$$

In Equation (1), the light fields have amplitudes $E_j$, frequencies $w_j$, wavevectors $\vec{k}_j$, and phases $\phi_j$, respectively. Both laser fields are detuned from the exited level $|i\rangle$ by $\Delta$. It is assumed that $\vec{E}_A$ only couples states $|g\rangle$ and $|i\rangle$, and likewise, that $\vec{E}_B$ only couples states $|e\rangle$ and $|i\rangle$. The Hamiltonian describing the three state system and laser fields is $H = H_0 + H_1$, where $H_0$ describes the unperturbed atom and electromagnetic field energy. The atom-field coupling Hamiltonian $H_1$ is given by:

$$H_1 = \frac{\hbar}{2}\begin{bmatrix} 0 & w_{ei}\exp(iw_B t) & 0 \\ w_{ei}^*\exp(-iw_B t) & 0 & w_{ig}^*\exp(-iw_A t) \\ 0 & w_{ig}\exp(iw_A t) & 0 \end{bmatrix} \qquad (2)$$

In Equation (2), $w_{mn}$ is the Rabi frequency corresponding to the coupling between levels m and n. The Rabi frequency is the frequency of population oscillation for a given atomic transition in a given light field. It is associated with the strength of the coupling between the light and the transition.

The density matrix P for the three-level system is given by:

$$\rho = \begin{bmatrix} \rho_{ee} & \rho_{ei} & \rho_{eg} \\ \rho_{ie} & \rho_{ii} & \rho_{ig} \\ \rho_{ge} & \rho_{gi} & \rho_{gg} \end{bmatrix} \qquad (3)$$

The equation of motion for ρ, including spontaneous emission as a loss term $\dot{\rho}_{SE}$ is given by:

$$\frac{d\rho}{dt} = \frac{1}{i\hbar}[H, \rho] + \dot{\rho}_{SE} \quad (4)$$

The loss term $\dot{\rho}_{SE}$ may be defined as follows:

$$\dot{\rho}_{SE} = \begin{bmatrix} \frac{\Gamma}{2}\rho_{ii} & -\frac{\Gamma}{2}\rho_{ei} & 0 \\ -\frac{\Gamma}{2}\rho_{ie} & -\Gamma\rho_{ii} & -\frac{\Gamma}{2}\rho_{ig} \\ 0 & -\frac{\Gamma}{2}\rho_{gi} & \frac{\Gamma}{2}\rho_{ii} \end{bmatrix} \quad (5)$$

In Equation (5), Γ is the average rate of spontaneous decay from the excited state (this model neglects other possible decoherence processes, such as collisions). In addition, a closed three-level system as been assumed, in which spontaneous emission necessarily returns atoms to the ground states that are addressed by the laser fields. This analysis can be readily extended to account for the more realistic case where atoms can also spontaneously decay to other ground state hyperfine levels which are not coupled by the fields, and are then lost from the populations of interest.

To reduce the dimensionality of the problem, the excited state may be adiabatically eliminated by setting $\dot{\rho}_{ei}=\dot{\rho}_{gi}=0$. This step assumes that the Raman detuning is much less than the detuning of the laser fields from the exited level (expressed in Equation (6) below) and that the excited state population is small compared to the ground state populations.

$$\delta=(w_A-w_B)-(w_e-w_g)\ll\Delta \quad (6)$$

Despite the elimination of the excited state, the effects of spontaneous emission carry through adiabatic elimination and alter the evolution of the reduced two state system, as discussed below.

As discussed above, the Bloch sphere provides a useful technique for visualizing two-level quantum systems. Accordingly, the two-dimensional density matrix may be recast in terms of a pseudospin on a Bloch sphere. This pseudospin $\vec{P}(t)$ may be defined in the laboratory frame with components given by Equation (7) below.

$$\vec{P}_i(t) = Tr\left[\begin{bmatrix} \rho_{ee} & \rho_{eg} \\ \rho_{ge} & \rho_{gg} \end{bmatrix} \cdot \sigma_i\right], i = x, y, z \quad (7)$$

In Equation (7), $\{\sigma_i\}$ are the Pauli spin matrices. Thus, the components of the pseudospin may be obtained as follows:

$$\begin{bmatrix} \vec{P}_x(t) \\ \vec{P}_y(t) \\ \vec{P}_z(t) \end{bmatrix} = \begin{bmatrix} 2\text{Re}[\rho_{eg}] \\ -2\text{Im}[\rho_{eg}] \\ \rho_{ee} - \rho_{gg} \end{bmatrix} \quad (8)$$

In order to determine an equation of motion for the pseudospin during a Raman pulse, the pseudospin $\vec{P}(t)$ may be transformed to the frame rotating with an effective drive field $\vec{\Omega}$ at the laser difference frequency $(w_A-w_B)$. In the rotating frame, the effective drive field is defined as:

$$\vec{\Omega}=\Omega\hat{\Omega}=\Omega[\cos\theta\hat{z}+\sin\theta(\cos\phi\hat{x}+\sin\phi\hat{y})] \quad (9)$$

In Equation (9), Ω is given by Equation (10) below and is the generalized two-photon Rabi frequency.

$$\Omega=\sqrt{|\Omega_{eff}|^2+(\delta_{AC}-\delta)^2} \quad (10)$$

In Equation (10), $\Omega_{eff}$ is the two-photon Rabi frequency, given by Equation (11) below, $\delta_{AC}=\Omega_{e,AC}-\Omega_{g,AC}$ is the differential AC Stark shift, and $\phi=\phi_A-\phi_B$ is the laser difference phase.

$$\Omega_{eff} = \frac{w_{ei}^* w_{gi}}{2\Delta} \quad (11)$$

Also in Equation (9):

$$\cos\theta = \frac{(\delta_{AC}-\delta)}{\Omega} \quad (12)$$

The pseudospin is transformed into the rotating frame by applying a rotation operator of the form $R[\vec{\alpha}]\equiv\exp(\alpha\cdot\hat{\alpha}\times)$:

$$\vec{P}_{rot}(t)=R[-(w_A-w_B)t\hat{z}]\vec{P}(t) \quad (13)$$

It can be shown that the equation of motion for $\vec{P}_{rot}(t)$ in the presence of the laser fields is:

$$\frac{d}{dt}\vec{P}_{rot}(t) - \vec{\Omega}\times\vec{P}_{rot} - \Gamma_{loss}\vec{P}_{rot} = -\hat{z}\Gamma_{source} \quad (14)$$

In Equation (14), $\Gamma_{loss}$ is the rate of coherence loss due to spontaneous emission (given by Equation (15) below), and $\Gamma_{source}$ is a polarization source rate to be described (given by Equation (16) below).

$$\Gamma_{loss} \equiv \frac{\Gamma(\Omega_{e,AC}+\Omega_{g,AC})}{2\Delta} \quad (15)$$

$$\Gamma_{source} \equiv \frac{\Gamma\delta}{2\Delta} \quad (16)$$

The first two terms on the left hand side of Equation (14) match the classical result for a spin precessing about an effective drive field vector. The two remaining terms, however, represent new dynamics introduced by spontaneous emission. While the term proportional to $\Gamma_{loss}$ simply causes decoherence, the term proportional to $\Gamma_{source}$ induces a population difference $P_z$ for non-zero Raman detuning.

According to one embodiment, it is demonstrated that the expression for the pseudospin after a Raman pulse of duration t is:

$$\vec{P}_{rot}(t)=e^{-\Gamma_{loss}t}R[\vec{\Omega}t]\cdot\vec{P}(0)+(e^{-\Gamma_{loss}t}-1)$$
$$\vec{P}_{asym}+[e^{-\Gamma_{loss}t}R[$$
$$\vec{\Omega}(t)]-1][(\Gamma_{loss}\cdot1-\Omega(\hat{\Omega}\times))^{-1}\cdot(\hat{z}\Gamma_{source})] \quad (17)$$

The first term on the right hand side of Equation (17) represents the standard result of a precessing polarization, but now with a decay rate associated with decoherence resulting from spontaneous emission. The term $\vec{P}_{asym}$ is the pseudospin reached asymptotically as t approaches infinity. For δ=0 and Δ<0, $\vec{P}_{asym}$ is given by:

$$\vec{P}_{asym} \equiv \frac{\Omega}{\Omega_{e,AC} + \Omega_{g,AC}} \hat{\Omega} \quad (18)$$

The expression above shows that a Raman pulse induces a polarization which is aligned with the effective drive field vector, thereby trapping population in a state that is decoupled from the light fields (i.e., a dark state). For Raman-resonant fields, the asymptotic polarization is a coherence at the laser difference phase, which clearly demonstrates coherent population trapping. Equations (17) and (18) also show that the trapped population increases proportionally to the pulse area, $\Omega t$. It should be noted that for the closed system considered in this derivation, the theory predicts that all of the population will eventually be trapped in the dark state. A more realistic theory including multiple excited states and the possibility of spontaneous emission to uncoupled ground state hyperfine levels would not lead to complete trapping, and for these reasons the model according to embodiments discussed herein gives an upper bound for CPT effects. These principles are further demonstrated in the examples discussed below.

According to certain embodiments, the principles discussed above may be used for controlled generation of hyperfine coherences and/or polarizations in cold atom clouds. According to one embodiment, the effective drive field may be pointed along any chosen direction, and thus a coherence and/or polarization may be induced in that direction via the coherent population trapping mechanism. Since very good control over the phase, detuning and duration of the effective drive field is generally achievable, these coherences and polarizations may be produced in a highly controlled manner. FIG. 7A illustrates a example, represented on a Bloch sphere, of a coherence 240 created without inducing a population difference by positioning the drive field vector 230 in the x-y plane. A population difference (polarization) may be induced using coherent population trapping by orienting the drive field vector 230 partially along the z-axis, as illustrated in FIG. 7B. In this example, the coherence vector 240 is similarly partially induced along the z-axis, indicating creation of a polarization in the system.

In one example, two Raman pulses separated by a predetermined time period may be used to generate a specific coherence and polarization. A first Raman pulse may be applied to rotate the initial polarization of the atoms about the x axis. For unpolarized atoms, the first Raman pulse induces a coherence in the x-y plane, aligned with the effective drive field, as discussed above and illustrated in FIG. 7A. For a first Raman pulse of tens of $\pi$ pulse durations in length, the initial polarization of the atoms is dispersed in the x-y plane by a spatially-varying Rabi frequency, and a coherence along the effective drive field vector is induced by coherent population trapping, as discussed above. The inhomogeneous Rabi frequency is produced by the intensity envelope of the Raman beams. To witness the induced coherence, a second Raman pulse may be applied after a brief dwell, much shorter than the coherence lifetime. In one example, the second Raman pulse is a $\pi/2$ pulse at a phase $\pm 90°$ relative to the first pulse. This second pulse rotates the coherently trapped population onto the z axis, as shown in FIG. 7B, where it may be measured as a population difference.

The density matrix presented above predicts that the trapped population scales with the pulse area, as is demonstrated in the examples discussed below. Accordingly, by controlling the orientation and duration of the applied Raman pulse(s), coherences and polarizations of selected phase and magnitude may be created. A series of interferometer experiments discussed in the examples below were used to characterize the dependence of CPT on Raman pulse duration, Raman detuning, Rabi rate, and laser detuning. Thus, by controlling these parameters, controlled exploitation of the coherent population trapping effect may be used to produce a continuum of precise coherences and/or polarizations. For example, given atoms in an unpolarized state, a Raman pulse of a known, selected duration can be used to induce a specific polarization proportional to the pulse duration. By contrast, the conventional optical pumping method of producing polarized atom samples can produce only single, uncalibrated values of polarization and coherence.

According to another embodiment, information may be extracted from a two level quantum system by measuring the populations of states A and B. In one embodiment, controlled generation of a CPT coherence may be used to provide a normalized population readout of the two quantum states. As discussed above, an applied Raman pulse may "torque" the initial atom polarization about its axis and induce a CPT coherence and polarization. A probe may be used to measure the z-component ($P_z$) over time of the ensemble. A second Raman pulse, 90 degrees out of phase with the first pulse, may then be applied to torque the induced polarization, as discussed above. The probe may record the z-component of the induced polarization over time. As discussed above, the induced polarization has a known magnitude based on the laser parameters of the applied effective drive field (i.e., the Raman pulses). This allows determination of the original polarization magnitude by comparing the initial state signal (measured with the probe) and the induced polarization signal.

Figure 8C:
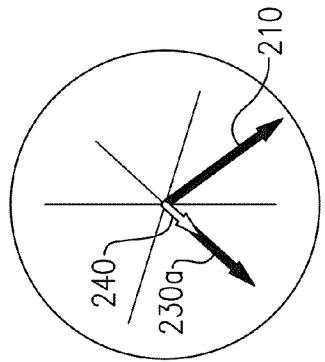
FIG. 8C is a diagram of the Bloch sphere of FIGS. 8A and 8B showing torquing of the population by the drive field and generation of a CPT coherence according to aspects of the invention.
Figure 8F:
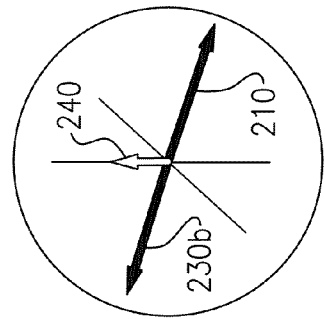
FIG. 8F is a diagram of the Bloch sphere of FIGS. 8A-8E illustrating rotation of the CPT coherence responsive to the second drive field pulse according to aspects of the invention.
Figure 8B:
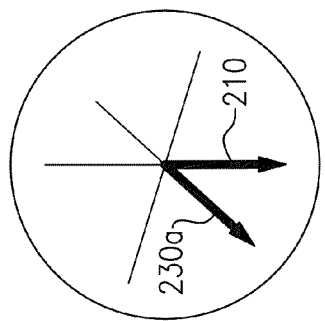
FIG. 8B is a diagram of the Bloch sphere of FIG. 8A showing an applied effective drive field according to aspects of the invention.
Figure 8E:
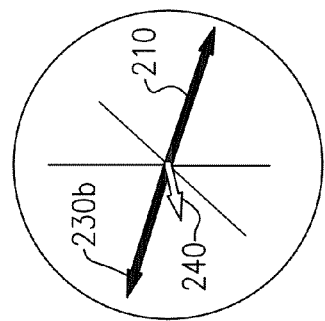
FIG. 8E is a diagram of the Bloch sphere of FIGS. 8A-8D illustrating application of a second drive field pulse according to aspects of the invention.
Figure 8A:
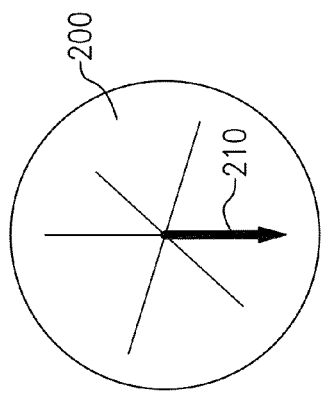
FIG. 8A is a diagram of a Bloch sphere showing an initial population in state B according to aspects of the invention.
Figure 8D:
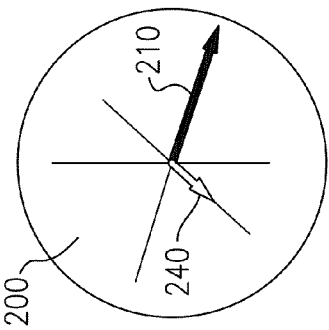
FIG. 8D is a diagram of the Bloch sphere of FIGS. 8A-8C illustrating the rotated population and induced CPT coherence at the end of the applied drive field pulse according to aspects of the invention.

Referring to FIGS. 8A-F, there is illustrated an example of using an induced CPT polarization to normalize measurement of an initial state polarization according to one embodiment. Consider an initial condition of a population in state B represented by state vector 201 and illustrated in FIG. 8A. A first Raman pulse may be applied to the system having a first effective drive field vector 230a, as illustrated in FIG. 8B. Referring to FIG. 8C, the drive field 230a torques the state vector 210 towards the equator of the Bloch sphere 200, while a CPT coherence 240 grows. At the end of the first Raman pulse, the state vector 210 and the coherence 240 are in the x-y plane, as illustrated in FIG. 8D. The population corresponding to the state vector 210 may be measured with a probe as discussed above. The CPT coherence 240 does not contribute to the population measurement. A second Raman pulse may then be applied to the system having a second effective drive field vector 230b, as shown in FIG. 8E. The second drive field 230b may have a known phase shift with respect to the first drive field 230a, as discussed above. The second drive field 230b torques the CPT coherence 240 toward the z-axis, as shown in FIG. 8E. When the CPT coherence 240 is aligned along the z-axis, as shown in FIG. 8F, the population may be measured again. Since the expected size of the CPT coherence population is known (as discussed above, the CPT effect scales with the laser properties in a known manner), it can be used to normalize the prior measurement of the state vector 210 population (FIG. 8D).

EXAMPLES

The function and advantages of these and other embodiments will be more fully understood from the following examples. The examples are intended to be illustrative in nature and are not to be considered as limiting the scope of the systems and methods discussed herein.

The examples discussed below use the following apparatus and cold Cesium atoms. Cesium atoms are loaded into a magneto-optic trap (MOT) from a thermal vapor. Loading occurs in 400 milliseconds (ms) in an octagonal quartz cell (2.75 inches diameter and 1.75 inches thickness) with nine fused viewports with $\lambda/20$ surfaces. A cesium vapor is produced by a getter source, with a background pressure of $<10^9$ torr. The trapping light is tuned to 12 MHz to the red of the $|6S_{1/2}F=4\rangle \rightarrow |6S_{3/2}F'=5\rangle$ cycling transition and collimated to a $1/e^2$ diameter of 10 mm before entering the cell (the intensity is $10I_{sat}$ ($I_{sat}$=1.1 mW/cm$^2$)). After loading the MOT, the atoms are cooled to 4 μK by polarization gradient cooling.

Once trapping is complete, the atoms are prepared in the magnetically insensitive $|F=3, m_F=0\rangle$ state for interferometry. After a 5 ms delay from extinction of the trapping light, during which stray magnetic fields decay, two magnetic coils introduce a vertical magnetic field of 0.5 G to lift the degeneracy of the Zeeman sublevels. Two laser beams resonant with the F=4→F'=4 and F=3→F'=4 transitions then optically pump 80% of the atoms into the $|F=4, m_F=0\rangle$ level in 75 μs. Subsequently, atoms in the magnetic-insensitive sublevel are transferred to the $|F=3, m_F=0\rangle$ state level by a microwave $\pi$ pulse. Residual population in the F=4 manifold is blown away from the MOT loading region by laser light resonant with the F=4→F'=5 cycling transition. Alternatively, for velocity sensitive interferometry in which colder ensembles are desirable, a velocity-selective Raman pulse is substituted for the microwave pulse to obtain samples with temperatures lower than 500 nK.

In these examples, laser beams for driving stimulated Raman transitions are generated from a distributed feedback laser emitting at 852 μm. The frequency of the laser is stabilized to a detuning of $\Delta=-1.25$ GHz from the F=4→F'=2 transition. To drive Raman transitions between the $|F=3, m_F=0\rangle$ and $|F=4, m_F=0\rangle$ hyperfine levels, the master laser light is phase modulated by an electro-optic modulator (EOM, Photline MPX850-NL10) at the hyperfine splitting frequency (9.193 GHz). For the chosen laser detuning, however, only one pair of sidebands (the carrier and first positive sideband) has a large two-photon Rabi frequency. The EOM modulation signal is generated by mixing a fixed 9.163 GHz signal and a phase- and frequency-tunable 30 MHz signal from an arbitrary waveform generator. To achieve short interferometer pulses, the modulated laser light is injected into a tapered amplifier. The differential AC Stark shift of the ground state levels is canceled by appropriately setting the intensity ratio of the light in the carrier frequency and first positive sideband. Pulse timing is controlled by switching the master laser light with an acousto-optic modulator before the EOM. The Raman beams are coupled into polarization-maintaining (PM) fiber and collimated to a $1/e^2$ full width of 1 cm before the vacuum cell.

To drive velocity sensitive Raman transitions, the beams are linearly polarized and retroreflected through a $\lambda/4$ wave plate that cross-polarizes the reflected light. Since both the upward and downward beams contain the two frequencies resonant with a Raman transition, two transitions with opposite $\vec{k}_{eff}=\vec{k}_A-\vec{k}_B$ are possible. Velocity insensitive transitions require substantially the same circular polarization in copropagating beams, and thus are not allowed (small imperfections in the polarization can still excite these transitions). As the atoms are released from the trap, the velocity acquired during free-fall lifts the degeneracy of the two resonances and, by choosing a drop time such that the resonances are Doppler shifted by more than the resonance linewidth, one $\vec{k}_{eff}$ can be selected. To preserve resonance with free-falling atoms, the Raman detuning is chirped (the chirp rate is $\vec{k}_{eff}$ g/(2π)≈23 kHz/ms for vertical beams). The retroreflected geometry is advantageous for interferometry because spurious phase differences introduced by wavefront aberrations are highly suppressed.

In the examples discussed below, the populations are measured by laser induced fluorescence. Raman transitions entangle the momentum state of the atoms with their internal state, and therefore each interferometer output is defined by one internal state of the atom. In these examples the interferometer phase is extracted by measuring the distribution of atom population in the $|F=3, m_F=0\rangle$ and $|F=4, m_F=0\rangle$ states at the output of the interferometer. At the end of the interferometer sequence, a probe beam resonant with F=4→F'=5 cycling transition irradiates the atoms for 500 μs and fluorescence from atoms in F=4 is collected (1.5%) and imaged on a high gain photodetector. The probe beam is retroreflected and red-detuned by 2 MHz to avoid pushing or heating atoms out of the detection region. Repump light is then pulsed for 100 μs to pump atoms in the F=3 level to the F=4 manifold. Since all of the atoms at this time are in F=4, a second cycling transition pulse provides a measure of the total population. Computing the ratio of the integrated fluorescence from the two pulses provides a normalized measure of the transition probability. This method may provide a signal-to-noise ratio of approximately 100. This approach differs from conventional population detection methods in that the detection of the CPT effects is accomplished with atom interferometry rather than, for example, measurements of resonance lineshapes with CPT-inducing pump-probe beams in a vapor cell.

Example 1

Velocity Insensitive Raman Pulses

For velocity insensitive Raman pulses, both frequencies of the bichromatic laser fields are applied to the atoms in the same direction, such that any Doppler shift experienced by the atoms due to difference in velocity between the atoms and the laser beams is essentially the same for both frequencies.

Example 1(a)

Figure 9:
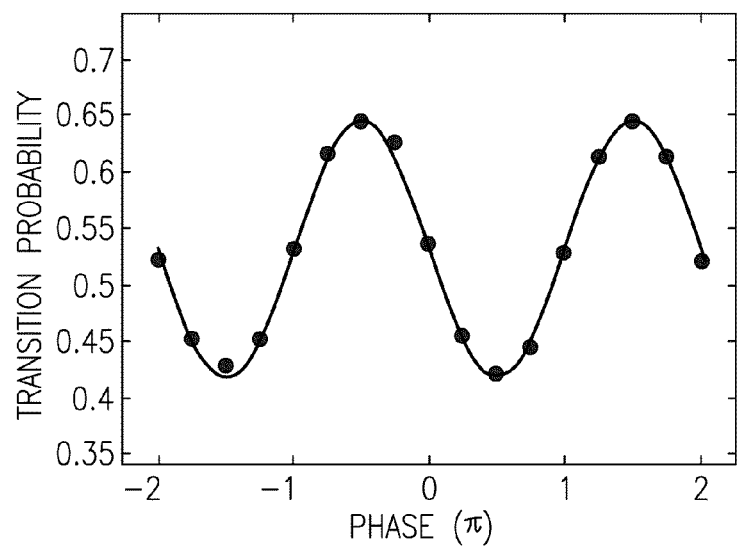
FIG. 9 is an interferogram measured by scanning the phase of a velocity-insensitive Raman pulse, demonstrating coherent population trapping according to aspects of the invention.

To distinguish coherently trapped population from population remaining in bright states, a Raman pulse with duration greater than $10t_\pi$ dephased the initial ensemble because of the inhomogeneous Rabi frequency produced by the intensity envelope of the Raman beams, as discussed above. At these pulse durations, the visibility of Rabi oscillations was less than 1% (in other words, $\langle P_z \rangle$=0 for the ensemble-averaged pseudospin and the average transition probability is approximately 50%). While the ensemble appears completely dephased, population trapped in a dark superposition state persists. By subsequently applying a $\pi/2$ pulse, as discussed above, this coherence produced an observable population difference which was maximized if the laser difference phase of the second pulse was ±90° relative to the phase of the first pulse. An interferogram measured by scanning the phase of the $\pi/2$ pulse is illustrated in FIG. 9. FIG. 9 illustrates a clear signature of CPT induced by the first Raman pulse.

Figure 10:
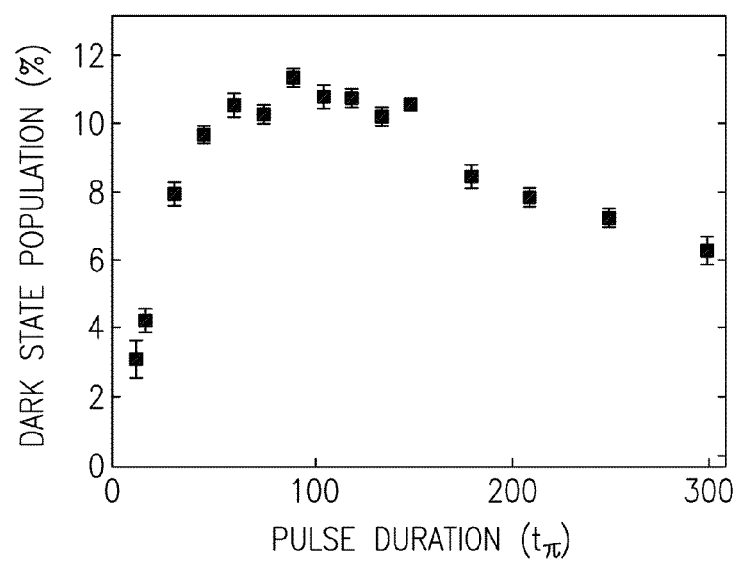
FIG. 10 is a graph illustrating an example of scaling of trapped population with Raman pulse duration according to aspects of the invention.
Figure 11:
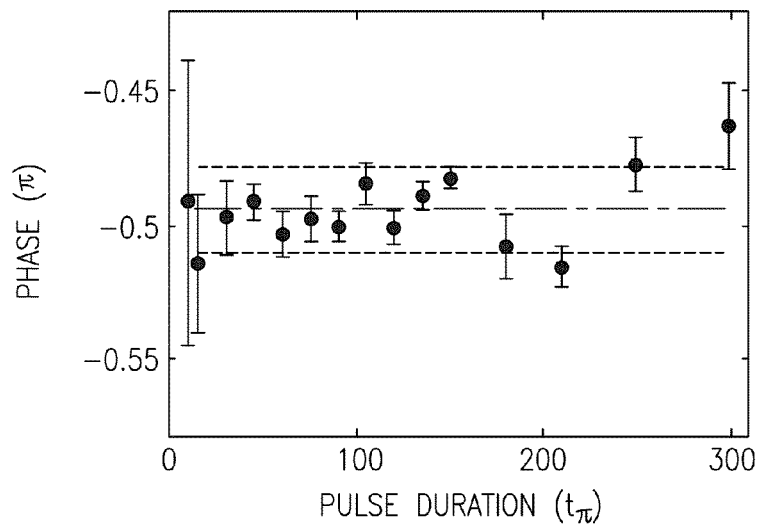
FIG. 11 is a graph illustrating the phase of dark state coherences induced by velocity insensitive Raman pulses as a function of pulse duration according to aspects of the invention.

Referring to FIG. 10, there is illustrated an example of measured dark state (trapped) population induced by resonant Raman pulses for a range of pulse durations. As discussed above, the trapped population scales with the pulse area, as demonstrated in this example. In FIG. 10, the pulse duration is scaled in units of $t_\pi$. Similar curves were observed with Rabi rates over a range of 20-100 kHz. For pulse areas less than $40\pi$, the trapped population increases approximately linearly. Trapping appears to saturate about 60-80π, and thereafter, losses due to spontaneous emission and weak coupling out of the dark state dominate. A linear fit over the low pulse area data estimates that a π pulse traps about 1.5% of the population for Δ=1.65 GHz. Direct measurements of CPT for Raman pulses with pulse areas under 10π were not achieved in this example because of inadequate scrambling of the initial ensemble. However, as illustrated in FIG. 11, the phase of the observed coherences at longer pulse durations remains at the expected phase of Δφ=π/2.

Figure 12:
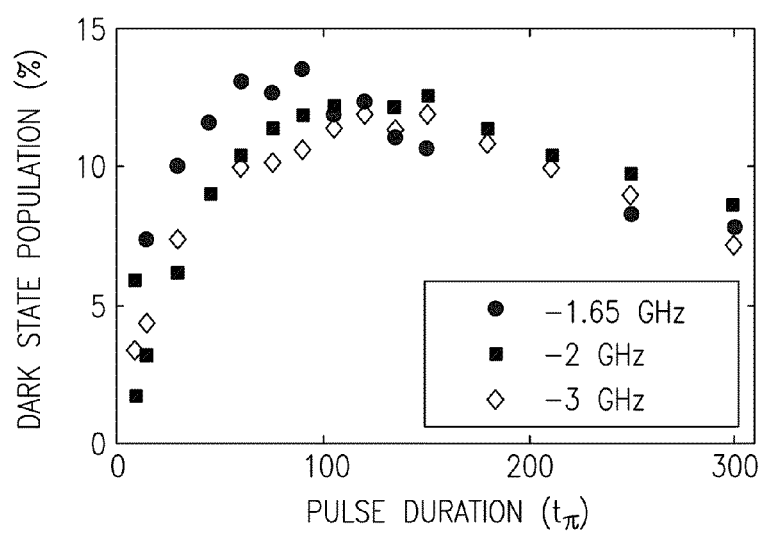
FIG. 12 is a graph illustrating induced tapped population (in percentage) as a function of pulse duration for several different Raman laser detunings, according to aspects of the invention.

FIG. 12 shows trapped population versus pulse duration curves for several laser detunings, from −1.25 to −3 GHz. While larger laser detuning ultimately suppresses CPT, increased spontaneous emission and the effect of multiple excited states also reduce trapping efficiency at small laser detunings In this example, a maximum trapping was observed for laser detunings of approximately −1.5 GHz. As illustrated in FIG. 12, the magnitude of the trapped population is weakly dependent on Raman laser detuning.

Example 1(b)

As discussed above, the induced polarization in the Bloch sphere is parallel (as opposed to anti-parallel) to the effective drive field for negative laser detunings To demonstrate this principle, in this example, the vertical component $P_z$ of the induced dark state population was measured as a function of Raman detuning, which points the effective drive field vector out of the x-y plane. In this example, an initial sample of atoms was prepared in the $|F=3, m_F=0\rangle$ state having $\vec{P}=-(z)$. A coherent superposition of the $|F=3, m_F=0\rangle$ and $|F=4, m_F=0\rangle$ levels was formed with a Raman π/2 pulse. After a brief dwell time (a few μs, for example), an off-resonant second Raman pulse is applied to dephase the initial coherence and induce a dark state polarization. In this example, the laser frequency difference frequency was changed between the first and second pulses by varying amounts and the laser difference phase for the second pulse was shifted such that the initial polarization was dispersed with an average transition probability of 50% (i.e., $P_z=0$). This phase offset for each Raman detuning was experimentally determined using a π/2−π* interferometer (π* denotes an off-resonant π pulse) with the same dwell time between pulses. The $P_z$ component of the trapped population was measured by reading out the population transfer and comparing to 50%. In order to suppress systematic errors resulting from drifting Raman beam power, $P_z=0$ was calibrated in every other measurement by applying a single resonant 15.5π pulse and measuring population transfer.

Figure 13:
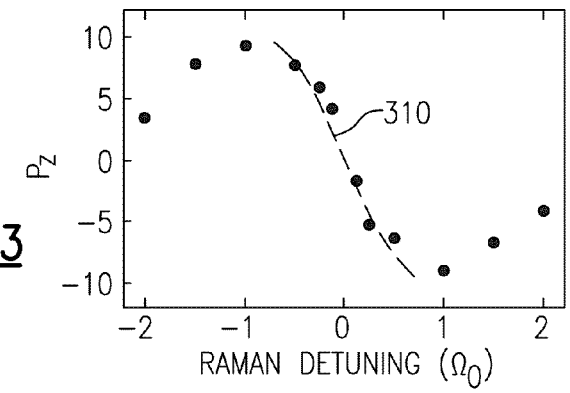
FIG. 13 is a graph illustrating measurements of $P_z$ of dark state population induced by off-resonant velocity insensitive Raman pulses according to aspects of the invention.

Referring to FIG. 13, there is illustrated a graph of measurements of $P_z$ of dark state population induced by off-resonant Raman pulses. The dashed line 310 represents the z-projection of the dark state polarization induced by a resonant Raman pulse, but which is aligned with the effective drive field for small Raman detunings FIG. 13 shows the induced population $P_z$ for Δ=−1.25 GHz and a second pulse duration of 40π. This dispersive profile has extrema at δR=±Ω₀. For δR<|Ω₀|, the observed $P_z$ resembles the z-projection of a polarization vector aligned with the effective drive field and with a magnitude equal to the population trapped by a resonant Raman pulse (≈9.5% for a 40π pulse). At larger Raman detunings, CPT effects are reduced. These measurements confirm the prediction of the density matrix presented above that population trapping induces a polarization parallel to the effective drive field vector.

Example 2

Velocity Sensitive Raman Pulses

Figure 1:
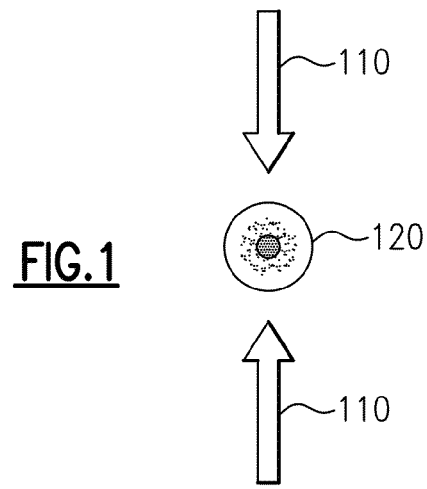
FIG. 1 is a schematic diagram illustrating application of a bichromatic laser drive field to an atom cloud.

For velocity sensitive Raman pulses, the two frequencies of the bichromatic laser fields are applied to the atom cloud in opposite directions (as illustrated in FIG. 1). As a result, the Doppler shift experienced by the atoms may be significantly different for the two laser beams. Velocity sensitive Raman transitions commonly serve as an atom beamsplitter in high precision experiments because they impart a factor of about $10^5$ more momentum than velocity insensitive Raman transitions, leading to larger interferometer phase shifts.

To detect effects of CPT with velocity sensitive Raman pulses, a slightly different method was used than that described above for velocity insensitive Raman pulses. The cold Cesium atoms were prepared in the $|F=3, m_F=0\rangle$ level and then a microwave π/2 pulse was applied. Since the wavelength of the microwave transition (~3.3 cm) is large compared to the cloud size (~1 mm), all of the atoms experienced a similar phase. Following a 3 ms dwell time, a long, resonant velocity sensitive Raman pulse dispersed the ensemble and induced CPT. The diffusion of the cloud ensured that the atoms diffused over a range of several effective wavelengths $(2\pi/|\vec{K}_{eff}|)$ during the dwell time, randomizing the phase difference between the microwave and Raman pulse across the ensemble. After a brief dwell time (typically 1-2 μs), a Raman π/2 pulse at variable phase produced an interferogram for measuring the trapped population.

Figure 14:
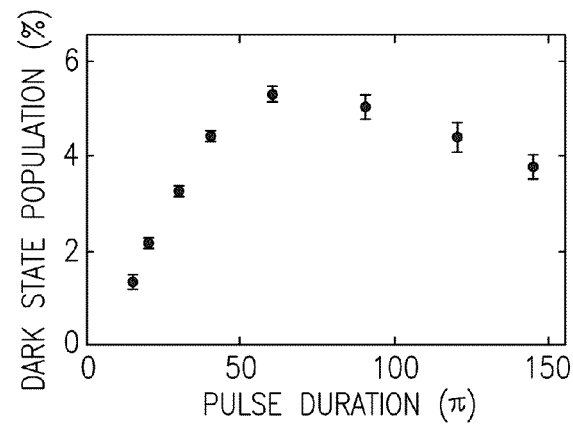
FIG. 14 is a graph illustrating measurements of $P_z$ of dark state population induced by off-resonant velocity sensitive Raman pulses according to aspects of the invention.

FIG. 14 illustrates the profile of dark state population versus pulse duration, for a laser de-tuning of Δ=−1.25 GHz and a Rabi rate of $\Omega_0/2\pi=80$ kHz. This curve resembles the measurements of dark state population for varying Raman pulse duration in the analogous velocity insensitive example (compare with FIG. 10). FIG. 14 illustrates that the CPT effect appears to saturate between 60-80 $t_\pi$ and decays at longer pulse durations, similar to the velocity-insensitive examples.

Figure 15:
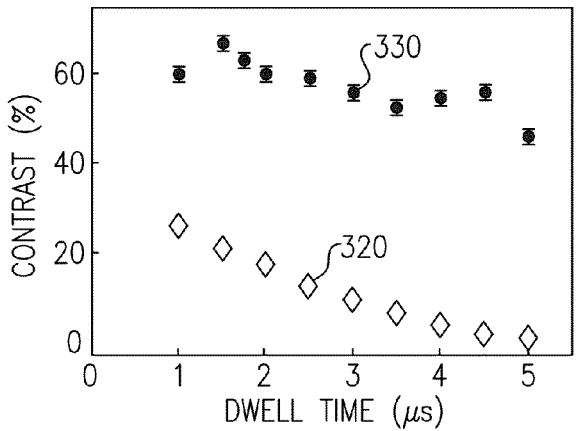
FIG. 15 is a graph illustrating contrast of a velocity sensitive π/2–π/2 interferometer measured for a range of dwell times, according to aspects of the invention.

While the magnitude of the dark state population appears smaller than what was measured with velocity insensitive beams, these measurements underestimate the trapped population because the interferometer is non-overlapping, and consequently exhibits poor phase contrast (the measure for the trapped population). To compensate for this inefficiency, the contrast of a velocity sensitive π/2−π/2 interferometer was measured for a range of dwell times. The results are illustrated in FIG. 15. The contrast of this non-overlapping interferometer indicates the efficiency with which the dark state population induced by velocity sensitive Raman pulses may be measured. Velocity selection suppresses decoherence due to cloud diffusion. Referring to FIG. 15, it can be seen that for a 7-9 μK cloud (curve 320), less than 30% contrast is obtainable. With velocity selection, however, atoms with a temperature of 300 nK produced greater than 55% contrast for the same interferometer (shown by the upper curve 330 in FIG. 15). In both cases, adjusting the measured dark state population by this two pulse interferometer visibility leads to an estimated maximum trapped population of about 9%, close to the maximum value observed with velocity-insensitive Raman pulses. Less efficient population trapping by velocity sensitive Raman pulses is expected due to the Doppler broadening of the resonance. Based on the slope in FIG. 14 at short pulse durations, an induced dark state population of 0.37% is estimated for a 1π pulse.

Thus, aspects and embodiments provide a density matrix representation which, by including spontaneous emission as a coherence loss rate, predicts coherent population trapping in a three-level atom. By performing adiabatic elimination on the excited state, the reduced two state system may be represented as a pseudospin precessing about an effective drive field on a Bloch sphere. This representation may be used to detect and manipulate CPT effects in atom interferometers. The examples presented above demonstrate that CPT may be measured in both velocity insensitive and velocity sensitive Raman pulse atom interferometry. Furthermore, the examples demonstrate the dependence of the induced dark state population on Raman pulse duration, two-photon Rabi frequency, laser detuning, and Raman detuning As a result, by controlling these parameters, known CPT coherences and polarizations may be generated in a controlled and precise manner. Thus, the principles disclosed herein provide a method for producing and manipulating coherences arising from CPT in cold atoms. These coherences may be used to generate precise, specific polarizations from initially unpolarized atoms, and to normalize population measurements as discussed above. Precision polarization reference may be exploited in numerous applications and devices employing atom interferometry, including, for example, atomic clocks and inertial sensors.

Having described above several aspects of at least one embodiment, it is to be appreciated various alterations, modifications, and improvements will readily occur to those skilled in the art. For example, an extension of the density matrix incorporating multiple excited states may address the effect of multiple possible dark states. In addition, direct measurements of trapped population at short pulse durations, such as approximately $10\pi$, may be achieved by scrambling the initial state with microwave transitions rather than Raman pulses. Such alterations, modifications, and improvements are intended to be part of this disclosure and are intended to be within the scope of the invention. Accordingly, the foregoing description and drawings are by way of example only.

What is claimed is:

1. A method of generating controlled hyperfine polarizations in a sample of cold atoms, the method comprising:
    applying a first Raman pulse having a first predetermined duration and phase to induce a coherence aligned with an effective drive field vector of the first Raman pulse;
    after a predetermined dwell time, applying a second Raman pulse having a second predetermined phase that is ±90 degrees relative to the first predetermined phase to rotate the induced coherence perpendicular to the effective drive field vector of the first Raman pulse; and
    measuring the induced coherence as a population difference.

2. The method of claim 1, wherein applying the first Raman pulse includes:
    selecting the first predetermined phase based on a desired phase of the induced coherence; and
    selecting the first predetermined duration based on a desired amplitude of the induced coherence.

3. The method of claim 1, wherein the first predetermined duration is at least ten $\pi$ pulse durations.

4. The method of claim 1, wherein the predetermined dwell time is less than a lifetime of the induced coherence.

5. The method of claim 1, wherein applying the second Rama pulse includes applying a $\pi/2$ Raman pulse.

6. The method of claim 1, wherein each of the first and second Raman pulses is applied using a bichromatic laser field.

7. The method of claim 6, wherein applying the first and second Raman pulses includes applying velocity insensitive Raman pulses.

8. The method of claim 6, wherein a laser difference for the first Raman pulses is different than a laser difference frequency for the second Raman pulse.

9. The method of claim 6, applying the first and second Raman pulses includes applying velocity sensitive Raman pulses.

10. A method of generating a precise polarization having a desired phase and magnitude from an initially unpolarized cold atom cloud, the method comprising:
    applying a Raman pulse having the desired phase to the atom cloud for a duration sufficient to produce an effective drive field and induce the precise polarization via coherent population trapping.

11. The method of claim 10, wherein applying the Raman pulse includes applying a velocity insensitive Raman pulse.

12. The method of claim 10, wherein applying the Raman pulse includes applying a velocity sensitive Raman pulse.

13. The method of claim 10, wherein applying the Raman pulse includes selecting a laser detuning frequency and laser detuning phase of the Raman pulse to achieve a desired orientation of the effective drive field.

14. A method of providing a normalized population readout in a two-state quantum system, the method comprising:
    applying a first Raman pulse having a first phase to the quantum system to induce precession of an initial polarization and to induce a first polarization via coherent population trapping;
    during the first Raman pulse, measuring a z-component of the initial polarization of the quantum system using a probe to obtain a first relative amplitude of the initial population and to dephase the initial population;
    applying a second Raman pulse having a second phase that is ±90 degrees relative to the first phase to rotate the first polarization;
    measuring a z-component of the first polarization using the probe to obtain a second relative amplitude of the first polarization;
    comparing the first and second relative amplitudes; and
    determining a magnitude of the initial polarization of the quantum system based on the comparison and on a known relationship between parameters of the first and second Raman pulses and a magnitude of the first polarization.

15. The method of claim 14, wherein applying the first Raman pulse includes applying a Raman pulse having a duration of at least ten $\pi$ pulse durations.

* * * * *